_United States Patent_ [19]

Kingsman

[11] Patent Number: 6,132,731

[45] Date of Patent: Oct. 17, 2000

[54] MURINE LEUKEMIA VIRUS VECTORS

[75] Inventor: Alan John Kingsman, Islip, United Kingdom

[73] Assignee: Oxford Biomedica (UK) Limited, Oxford, United Kingdom

[21] Appl. No.: 08/930,503

[22] PCT Filed: Apr. 1, 1996

[86] PCT No.: PCT/GB96/00776

§ 371 Date: Oct. 8, 1997

§ 102(e) Date: Oct. 8, 1997

[87] PCT Pub. No.: WO96/31602

PCT Pub. Date: Oct. 10, 1996

[30] Foreign Application Priority Data

Apr. 1, 1995 [GB] United Kingdom .................. 9506782

[51] Int. Cl.$^7$ .......................... C07H 21/02; C07K 14/15; C12N 7/01

[52] U.S. Cl. ..................... 424/207.1; 424/199.1; 424/93.1; 424/187.1; 424/192.1; 435/235.1; 435/325; 435/357; 435/5; 435/320.1; 514/44; 530/350; 530/300; 530/388.35; 536/23.1; 536/23.4; 536/23.72

[58] Field of Search ............... 424/199.1, 207.1, 424/93.1, 187.1, 192.1; 435/235.1, 325, 357, 5, 320.1; 514/44; 530/350, 300, 388.35; 536/23.1, 23.4, 23.72

[56] References Cited

FOREIGN PATENT DOCUMENTS

94/11524  5/1994  WIPO.

OTHER PUBLICATIONS

Valesia Wittmann et al. J Virol. vol. 68, No. 7, Jul. 1994, p 4609–4619.

Jones et al. Nature. vol. 373. Feb. 9, 1995, p 539–544.

_Primary Examiner_—Phuong T. Bui
_Attorney, Agent, or Firm_—Wenderoth, Lind & Ponack, L.L.P.

[57] ABSTRACT

A proteinaceous particle comprises a capsid enveloped by ecotropic Murine Leukemia virus envelope proteins characterized in that a heterologous peptide which binds to a non-murine cell is inserted in, entirely replaces, or replaces a portion of the native Ser-Gly-Gly-Ser-Ser-Pro-Gly of the VRA region of said envelope proteins. A method for preparing a plurality of such proteinaceous particles comprises expressing within a host cell (i) self-assembling capsid proteins, (ii) Murine Leukemia virus envelope proteins, said ENV proteins modified as defined, and optionally, (iii) packageable RNA, and then culturing the host cells and harvesting the resultant budded particles.

12 Claims, 4 Drawing Sheets

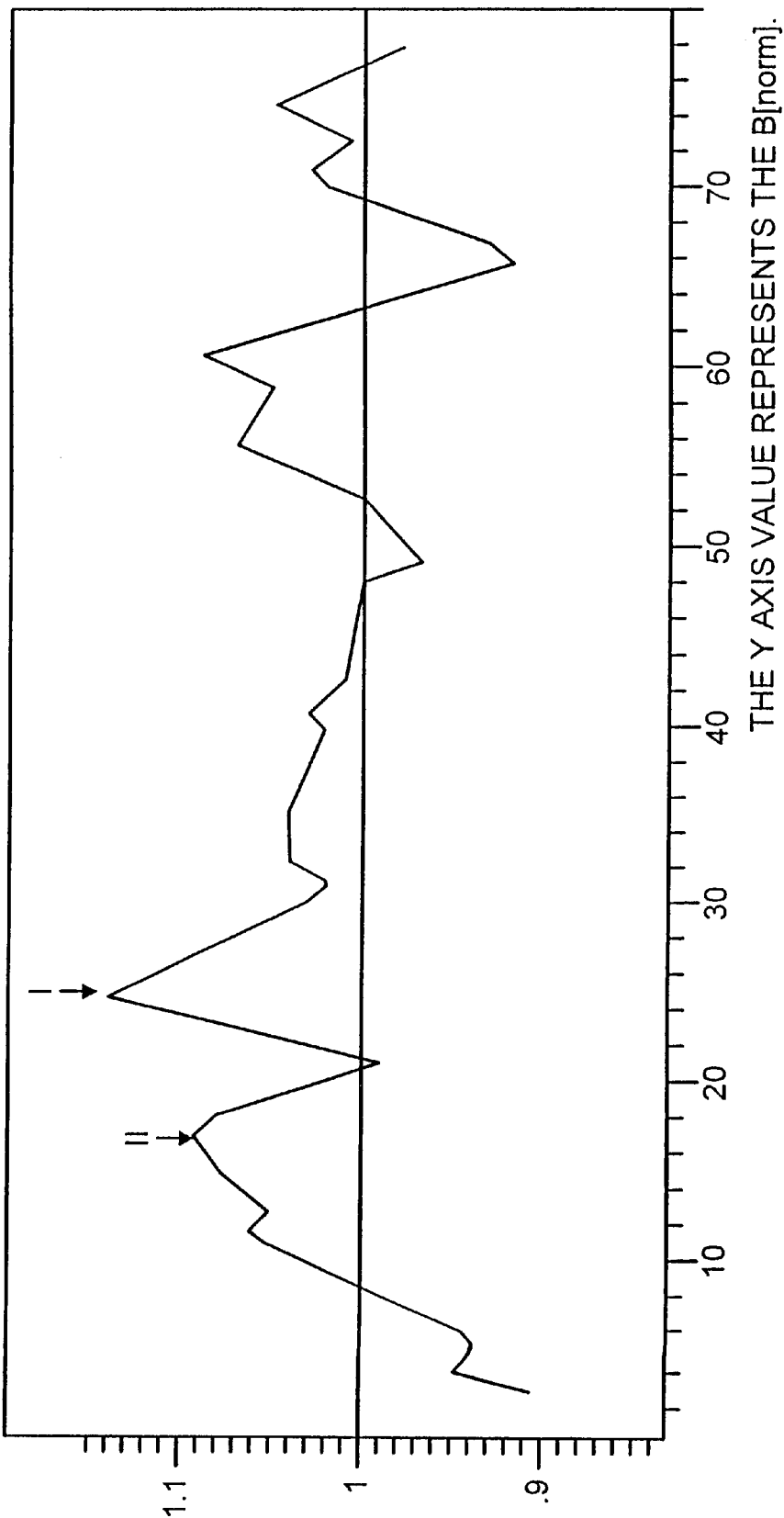

Multiple Sequence Alignment.

|  | 1 |  |  |  |  |  |  |  |  |  |  |  |  | 14 |
|---|---|---|---|---|---|---|---|---|---|---|---|---|---|---|
| Ecotropic Envelope: | His | Gly | Pro | Ser | Tyr | Trp | Gly | Leu | Glu | Tyr | Gln | Ser | Pro | Phe |
| Amphotropic Envelope: | ... | Val | Gly | Glu | Glu | Trp | Asp | ... | ... | ... | ... | ... | ... | ... |
| Polytropic Envelope: | ... | Ile | Gly | Glu | Glu | Trp | Glu | ... | ... | ... | ... | ... | ... | ... |
| Xenotropic Envelope: | ... | Val | Gly | Asp | His | Trp | Glu | ... | ... | ... | ... | ... | ... | ... |

|  |  |  |  |  |  |  |  |  |  |  |  |  |  |  |  |  |  | 32 |
|---|---|---|---|---|---|---|---|---|---|---|---|---|---|---|---|---|---|---|
| Ser | Ser | Pro | Gly | Pro | Pro | Cys | Cys | Ser | Gly | ... | ... | ... | Gly | Ser | Ser | Pro | Gly | Cys | Ser |
| ... | ... | ... | ... | ... | ... | ... | ... | ... | ... | Pro | Ser | Asp | Gln | Glu | Pro | Tyr | Val | Gly |
| ... | ... | ... | ... | ... | ... | ... | ... | ... | ... | ... | Glu | Thr | ... | ... | ... | ... | ... | Gly |
| ... | ... | ... | ... | ... | ... | ... | ... | ... | ... | ... | Asp | Pro | Glu | Pro | Asp | Ile | Gly |

|  |  |  |  |  |  |  |  |  |  |  |  |  |  |  |  | 52 |
|---|---|---|---|---|---|---|---|---|---|---|---|---|---|---|---|---|
| Arg | Asp | Cys | Glu | Glu | Pro | Leu | Thr | Ser | Leu | Thr | Pro | Arg | Cys | Asn | Thr | Ala | Trp | Asn | Arg |
| Tyr | Gly | Cys | Lys | Tyr | Pro | ... | ... | ... | ... | ... | ... | ... | ... | ... | Ala | Gly | Arg | Gln | Arg |
| Leu | Gly | Cys | Arg | Thr | Pro | ... | ... | ... | ... | ... | ... | ... | ... | ... | Gly | Gly | Arg | Lys | Arg |
| Asp | Gly | Cys | Arg | Ser | Pro | ... | ... | ... | ... | ... | ... | ... | ... | ... | Gly | Gly | Arg | Lys | Arg |

|  |  |  |  |  |  |  |  |  |  |  |  |  |  |  |  |  |  |  | 72 |
|---|---|---|---|---|---|---|---|---|---|---|---|---|---|---|---|---|---|---|---|
| Leu | Lys | Leu | Asp | Gln | Thr | Thr | His | Lys | Ser | Asn | Glu | Gly | Phe | Tyr | Val | Cys | Pro | Gly | Pro |
| Thr | Arg | Thr | Phe | Glu | ... | ... | ... | ... | ... | ... | ... | ... | Phe | Tyr | Val | Cys | Pro | Gly | His |
| Ala | Arg | Thr | Phe | Glu | ... | ... | ... | ... | ... | ... | ... | ... | Phe | Try | Val | Cys | Pro | Gly | His |
| Ser | Arg | Leu | Tyr | Glu | ... | ... | ... | ... | ... | ... | ... | ... | Phe | Tyr | Val | Cys | Pro | Gly | His |

| His | Arg | Pro | Arg | Glu | Ser | Lys | Ser | (SEQ. I.D. NO. 16) |
|---|---|---|---|---|---|---|---|---|
| Thr | Val | Lys | ... | ... | ... | Ser | Gly | (SEQ. I.D. NO. 17) |
| Thr | Val | Pro | ... | ... | ... | Thr | Gly | (SEQ. I.D. NO. 18) |
| Thr | Val | Pro | ... | ... | ... | Ile | Gly | (SEQ. I.D. NO. 19) |

\* Bold letter: unconserved residues

FIG. 2

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
      (A) LENGTH: 7 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO: 1:

Ser Gly Gly Ser Ser Pro Gly
1               5

(2) INFORMATION FOR SEQ ID NO: 2:

(i) SEQUENCE CHARACTERISTICS:
      (A) LENGTH: 9 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO: 2:

Cys Thr Ile Asp Ser Pro Leu Asn Cys
1               5

(2) INFORMATION FOR SEQ ID NO: 3:

(i) SEQUENCE CHARACTERISTICS:
      (A) LENGTH: 16 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO: 3:

Cys Gln Gly Ala Thr Phe Ala Leu Arg Gly Asp Asn Pro Gln Gly Cys
1               5                   10                  15

(2) INFORMATION FOR SEQ ID NO: 4:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 4:

GCCGAATTCA TGGCGCGTTC AACGCTCTCA AAA      33

(2) INFORMATION FOR SEQ ID NO: 5:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 5:

GACCGAATTC CTATCTGAGT CGGATCCCAA ATG                                33

(2) INFORMATION FOR SEQ ID NO: 6:

(i) SEQUENCE CHARACTERISTICS:
             (A) LENGTH: 60 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO: 6:

ACCTTGGGGA TTATCGCCTC TTAAGGCAAA AGTAGCACCT TGGCAACAAG GGGGCCCCGG    60

(2) INFORMATION FOR SEQ ID NO: 7:

(i) SEQUENCE CHARACTERISTICS:
             (A) LENGTH: 60 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO: 7:

CAAGGTGCTA CTTTTGCCTT AAGAGGCGAT AATCCCCAAG GTTGTTCCAG AGACTGCGAA    60

(2) INFORMATION FOR SEQ ID NO: 8:

(i) SEQUENCE CHARACTERISTICS:
             (A) LENGTH: 7 amino acids
             (B) TYPE: amino acid
             (C) STRANDEDNESS:
             (D) TOPOLOGY: linear (ii) MOLECULE TYPE: peptide (xi) SEQUENCE DESCRIPTION: SEQ ID NO: 8:

Ser Ser Pro Pro Gly Pro Pro
 1               5

(2) INFORMATION FOR SEQ ID NO: 9:

(i) SEQUENCE CHARACTERISTICS:
             (A) LENGTH: 69 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO: 9:

ACCTTGGGGA TTATCGCCTC TTAAGGCAAA AGTAGCACCT TGACAAAAAG GGGATTGATA    60

TTCTAGCCC                                                           69

(2) INFORMATION FOR SEQ ID NO: 10:

(i) SEQUENCE CHARACTERISTICS:
             (A) LENGTH: 72 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO: 10:

TGTCAAGGTG CTACTTTTGC CTTAAGAGGC GATAATCCCC AAGGTTGTTG CTCAGGGGGC    60

AGCAGCCCAG GC    72

(2) INFORMATION FOR SEQ ID NO: 11:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

ATTCAGGGGG GAATCAATTT GAGTGCACAA GGGGGCCCCG G    41

(2) INFORMATION FOR SEQ ID NO: 12:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

ACTCAAATTG ATTCCCCCCT GAATTGTTCC AGAGACTGCG AA    42

(2) INFORMATION FOR SEQ ID NO: 13:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

ATTCAGGGGG GAATCAATTT GAGTACAAAA AGGGGATTGA TATTCTAGCC C    51

(2) INFORMATION FOR SEQ ID NO: 14:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

ACTCAAATTG ATTCCCCCCT GAATTGTTGC TCAGGGGGCA GCAGCCCAGG C    51

(2) INFORMATION FOR SEQ ID NO: 15:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 15:

Arg Gly Asp Ser
1

(2) INFORMATION FOR SEQ ID NO: 16:

(i) SEQUENCE CHARACTERISTICS:
        (A) LENGTH: 80 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 16:

His Gly Pro Ser Tyr Trp Gly Leu Glu Tyr Gln Ser Pro Phe Ser Ser Pro Pro
1               5                   10                  15

Gly Pro Pro Cys Cys Ser Gly Gly Ser Ser Pro Gly Cys Ser Arg Asp Cys Glu
        20              25                  30                  35

Glu Pro Leu Thr Ser Leu Thr Pro Arg Cys Asn Thr Ala Trp Asn Arg Leu Lys
            40              45                  50

Leu Asp Gln Thr Thr His Lys Ser Asn Glu Gly Phe Tyr Val Cys Pro Gly Pro
55              60                  65                  70

His Arg Pro Arg Glu Ser Lys Ser
        75              80

(2) INFORMATION FOR SEQ ID NO: 17:

(i) SEQUENCE CHARACTERISTICS:
        (A) LENGTH: 43 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 17:

Val Gly Glu Glu Trp Asp Pro Ser Asp Gln Glu Pro Tyr Val Gly Tyr Gly Cys
1               5                   10                  15

Lys Tyr Pro Ala Gly Arg Gln Arg Thr Arg Thr Phe Glu Phe Tyr Val Cys Pro
        20              25                  30                  35

Gly His Thr Val Lys Ser Gly
                40

(2) INFORMATION FOR SEQ ID NO: 18:

(i) SEQUENCE CHARACTERISTICS:
        (A) LENGTH: 37 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 18:

Ile Gly Glu Glu Trp Glu Glu Thr Gly Leu Gly Cys Arg Thr Pro Gly Gly Arg
1               5                   10                  15

Lys Arg Ala Arg Thr Phe Glu Phe Tyr Val Cys Pro Gly His Thr Val Pro Thr
        20              25                  30                  35

Gly (2) INFORMATION FOR SEQ ID NO: 19:

(i) SEQUENCE CHARACTERISTICS:

-continued

```
        (A) LENGTH: 41 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 19:

Val Gly Asp His Trp Glu Asp Pro Glu Pro Asp Ile Gly Asp Gly Cys Arg Ser
1               5                   10                  15

Pro Gly Gly Arg Lys Arg Ser Arg Leu Tyr Glu Phe Tyr Val Cys Pro Gly His
        20                  25                  30                  35

Thr Val Pro Ile Gly
                40
```

MURINE LEUKEMIA VIRUS VECTORS

FIELD OF THE INVENTION

This invention relates to a proteinaceous particle comprising a capsid, optionally containing nucleic acid, the capsid being enveloped by proteins adapted to target and deliver the particle to a desired host cell. Methods and materials for the preparation of such particles, and pharmaceutical compositions containing them, are also part of the invention. Such particles find application in immunology and gene delivery (gene therapy).

BACKGROUND OF THE INVENTION

Proteinaceous particles of the same order of magnitude as virions, which have affinity for particular cell types are potentially useful as delivery vehicles for bringing a desired therapeutic molecule carried by the particles into contact with cells of that type. The therapeutic molecule may be, for example, an antigen capable of stimulating a target cell of the immune system, or nucleic acid for incorporation within the target cell, the latter objective being a minimum requirement for successful gene therapy applications.

The use of recombinant retroviruses as vehicles in gene therapy is gaining increasing support. Natural retroviruses comprise a GAG protein "core" or "capsid", these terms being used interchangeably, the capsid being enveloped by the envelope proteins (strictly these are glycoproteins but will be referred to herein simply as envelope proteins), and within the capsid is packaged the viral genomic RNA. By application of recombinant nucleic acid technology, the structure of the capsid and envelope proteins, and of the genomic RNA, of a natural retrovirus may be altered. Thus, recombinant particles comprising capsid and envelope proteins can be used to carry foreign nucleic acid, for insertion into cells which are members of the host range defined by the receptor binding specificity of the envelope proteins. A major goal in retroviral gene therapy is to alter the host range of recombinant retroviral particles to target the particles to particular cell types and to provide efficient transduction. The preferred virus for developing retroviral gene therapy is generally accepted to be murine leukemia virus (MLV).

Outside the specific area of gene therapy, it would also be desirable to adapt proteinaceous particles for targeting to specific cell types, for example to deliver specific antigens to target cells of the immune system by presenting such antigens on proteinaceous virion-like particles whose envelope proteins carry sequences having an affinity for the desired target cell type.

Specific interactions have been proposed between the transmembrane (TM) domain of envelope (ENV) proteins and the matrix (MA) domain of GAG protein for selective incorporation of the envelope proteins into the self-assembling particle. In addition, the cell receptor binding domain of retroviral envelope proteins has been located near the N-terminus. In MLV, two discontinuous receptor recognition regions termed VRA and VRB have been identified (Battini et al. (1992) J. Virol. 66:1468–1475)). Any modification of the envelope protein to confer specific cell targeting properties on an enveloped capsid must retain the regions important for incorporation of the envelope, yet possess an altered receptor binding domain for targeted infection.

The use of targeted retroviral particles as carriers has been attempted before. Young et al. (1990) attempted to selectively incorporate CD4 into ALV particles by fusing CD4 to a truncated viral envelope protein. Curiously, there was incorporation of wild-type CD4 but very poor incorporation of the fusion protein. The absolute efficiency of incorporation was difficult to determine, and it is possible that both wild-type and fusion CD4 were poorly picked up by the virus.

In WO 94106920, retrovirus particles displaying a functional antibody fragment is disclosed. These inventors fused the gene coding for a functional antibody fragment (250 amino acids) at the 5'-end of the gene coding for the complete Moloney Murine Leukemia Virus envelope protein (Pr80env) and following transfection in an ecotropic packaging cell line recovered particles with specific hapten binding properties. That such modified viruses can infect cells using antibody-hapten recognition has not yet been demonstrated.

In WO 94/11524 the receptor binding region of the envelope protein of murine leukemia viruses were replaced by the mature rabbit alpha-1 acid glycoprotein antigen binding site region of an antibody.

In the foregoing publications,.wherein the envelope proteins have undergone gross changes, problems arose such as incorrect processing and transport of modified envelope proteins, low-level infectivity, poor envelope incorporation on the particle, or low viral titers on expression. It therefore appears that in order to maintain the envelope functions, other than cell targeting, i.e. correct processing and transport to the cell surface, incorporation onto the capsid particle, infection of the targeted cell and good expression yields, there should be minimal disruption to the envelope protein.

Valsesia-Wittmann et al. (J.Virol 68: 4609; 1994) used the 16 amino acid FLA-16 RGD peptide inserted into the strictly avitropic RSV envelope at specific sites to redirect tropism. Some insertion sites destroyed the ability of the envelope to be processed or incorporated in viral particles, and the most successful insertion site enabled the mutant virus produced to infect mammalian cells, but only at very low titres, namely $10^2$/ml, or $10^3$/ml when the virus was deglycosylated.

BRIEF DESCRIPTION OF THE INVENTION

The present invention is based on the identification by the present inventors of a specific site within the VRA region of ecotropic MLV envelope protein which can be modified by the incorporation of heterologous peptide sequences having affinity for cell types outside the normal host range of the ecotropic MLV, with minimal modification to the native envelope protein. Proteinaceous particles comprising capsids enveloped by such modified envelope proteins are expressed in high yield, are efficiently targeted to cell types carrying the counter-ligand to the inserted peptide, and can result in high levels of transduction of such cells.

DETAILED DESCRIPTION OF THE INVENTION

Figure 3:
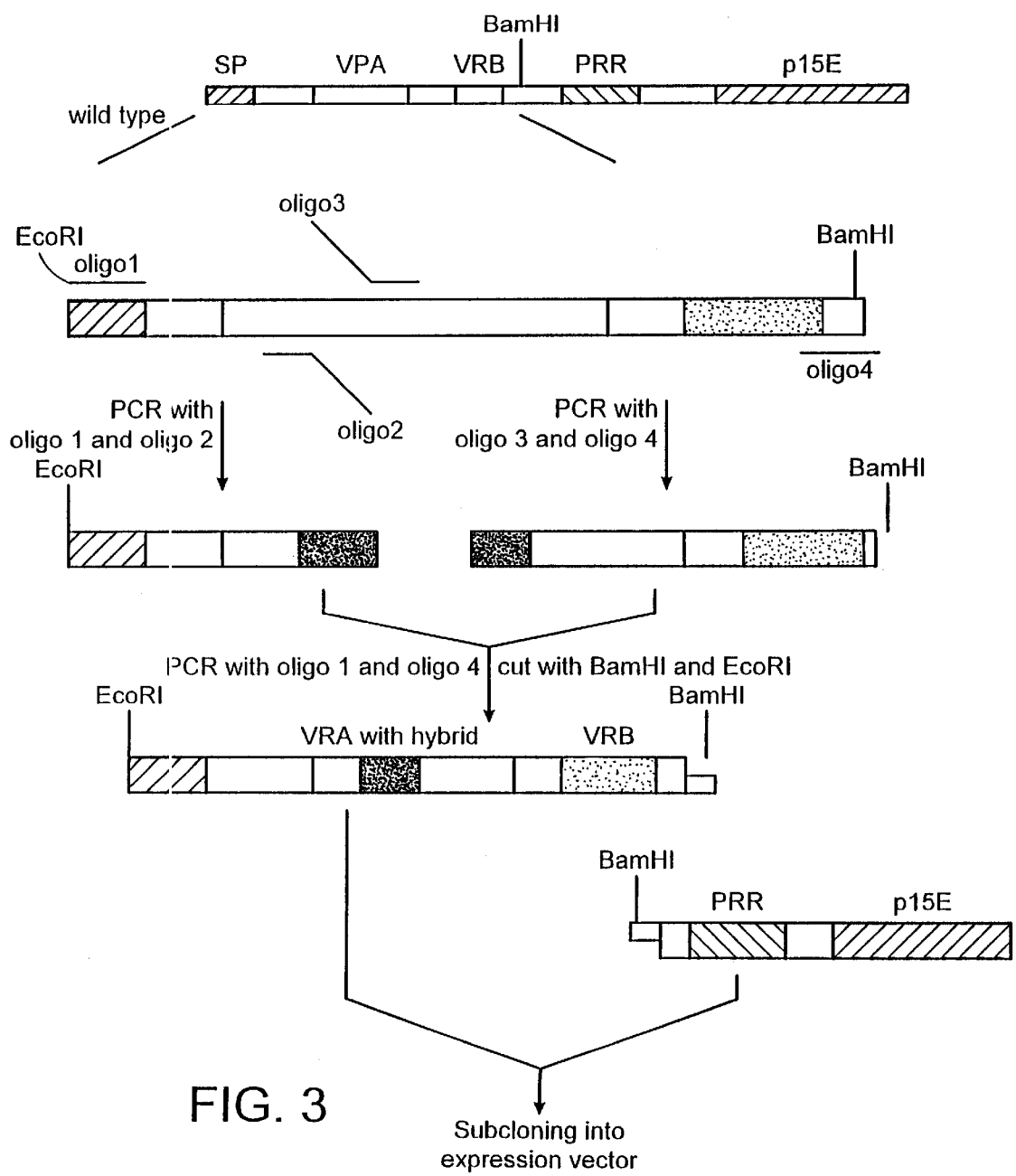

Thus the present invention provides a proteinaceous particle comprising a capsid enveloped by ecotropic Murine Leukemia Virus ("MLV") envelope proteins characterised in that a heterologous peptide which binds to a non-murine mammalian cell is inserted in, entirely replaces, or replaces a portion of the native SEQ ID NO: 1 of the VRA region of said envelope proteins.

The capsid may carry nucleic acid, for example packaged RNA which when released into the intracellular cytoplasm of the said non-murine mammalian cell is converted by reverse transcription into double stranded DNA, integrated into the host cell genomic DNA and subsequently expresses a therapeutic peptide or protein encoded by the packaged nucleic acid.

The invention is not limited to particles enveloped by MLV envelope proteins which are modified solely by the incorporation of the said peptide. In addition to the incorporation of the said peptide, the MLV envelope protein (and/or the capsid protein) may include a second peptide sequence having a desired biological utility such as antigenic or immunogenic activity.

For the purposes of this specification, the VRA region of MLV envelope protein is the sequence from position amino acid position 84 to position 163 of the sequence published in Shinnick et al. (1981) Nature. 293:543–548.

The native sequence within the said VRA region identified for insertion in, entirely replacing, or replacing a portion of, with a heterologous peptide capable of binding to a cell surface marker present on a mammalian cell other than a murine cell is -Ser-Gly-Gly-Ser-Ser-Pro-Gly-(SEQ ID NO: 1). This sequence is flanked by cysteine residues which may be capable of forming a disulphide bond causing the intervening sequence to form a surface exposed loop structure.

The term "capsid" as used herein means a particulate body formed by self assembly of a plurality of self-assembling retroviral GAG protein molecules or a plurality of self assembling protein molecules substantially homologous with retroviral GAG protein molecules.

The term "capsid protein" as used herein means a self-assembling retroviral GAG protein, or a self assembling protein substantially homologous with retroviral GAG protein. Capsid proteins include truncated and sequence modified forms of natural retroviral GAG protein molecules.

Pseudotyping is a natural phenomenon whereby co-infection of a cell with two different types of enveloped virus can result in the generation of infectious virus particles composed of the capsid proteins from one virus and the envelope proteins of the other. There are a number of reports of forced pseudotypes, McGuigan et al. (Vaccine. Vol. 11 issue 6: 675–678; 1993) generated simian immunodeficiency virus (SIV) virus-like particles enveloped by the herpes simplex virus gD glycoprotein. In the Valsesia-Wittmann paper (ibid), the amphotropic MLV envelope was incorporated onto the rous sarcoma virus (RSV) capsid. Thus capsids present in particles of the invention are not limited to those which are the natural partners of any particular natural ecotropic MLV envelope protein However, in a preferred embodiment of the invention, the capsid protein is, or is substantially homologous with, an MLV GAG protein.

The term "substantially homologous with" as used herein means at least 70%, and preferably at least 80%, 90% or 95% homologous with the protein in question. Nucieic acid encoding a molecule which is substantially homologous with retroviral GAG proteins may hybridise with nucleic acid coding for a natural retroviral GAG protein (or would do so but for the degeneracy of the genetic code), for example under stringent conditions (such as at 35° C. to 65° C. in a salt solution of approximately 0.9M).

Peptides for use in the present invention are those which bind to non-murine mammalian cell types. Preferably they should be the minimum length consistent with effective target cell binding of particles of the invention incorporating them. They are preferably of a length not more than about three or four times that of the native SEQ ID NO: 1 which they replace, or partially replace, or into which they are inserted, for example not more than 30, 25, 20, 15, 10, 9, 8 or 7 amino acids. However, it is possible that longer molecules such as single chain antibodies, will also be suitable for use in the invention. The term "peptides" as used herein is therefore not intended to exclude these longer molecules, provided that the resulting envelope protein is not so disrupted that the proteinaceous particle can no longer perform the desired function eg. transduction. The integrity of an envelope protein containing a heterologous peptide can be easily tested by methods known in the art.

Suitable such peptides are those capable of binding integrin molecules. The integrins are a family of receptor molecules (also called integrin adhesion receptors) present on the surface of many cell types. Some integrins present on the cell surface can act as viral binding targets to allow attachment and integration of viruses. Many cellular adhesive proteins (substrate adhesion molecules) contain the tripeptide Arg-Gly-Asp (RGD) as the recognition sequence for protein-cell interactions. The list of receptor molecules and peptides which these recognise is ever increasing, Soria (Biotechnol. Appl. Biochem. 11 :527–551; 1989) reviews a number of these and other cell-cell, protein-cell interactions. Another suitable peptide for use in the invention is the Melanoma stimulating hormone peptide (Murphy et al. (1986) Proc. Natl. Acad. Sci. U.S.A. 83:8258–8263).

Examples of particular peptides for use in the present invention are those derived from VCAM-1, which bind to a non-murine mammalian cells, particularly the 9 amino acid VCAM-1 derived peptide (SEQ ID NO: 2; Jones, E. Y. et al. (1995) Nature. 373:539–544) capable of binding to the VLA-4 receptor, and the 16 amino acid peptide FLA16 (SEQ ID NO: 3, an -RGD-peptide) capable of binding to VLA-3 and VLA-5 receptors (Aumailley et al. (1990) FEBS Lett. 262:82–86). However, other peptides may equally be used.

Targeting therapeutic genes to selected integrins may have therapeutic value. For example, VCAM mediated delivery of anti-HIV genes to lymphocytes via VLA4 may provide a viable alternative to targeting through the gp120/CD4 interaction. In addition, some tumours, such as melanomas and lymphomas express high levels of VLA4 suggesting that anti-tumour genes might also be delivered through this receptor. The invention could be used for vaccine design or the expression and analysis of receptors or other membrane proteins. The invention could also be used towards the targeting of therapeutic genes to virus infected cells, genetically deficient cells or haematopoietic cells. In addition, it might be used for the delivery of genes to antigen presenting cells in order to stimulate MHC class I mediated cellular immune responses.

The finding of the present inventors that peptides as small as 9 amino acids are capable of efficiently redirecting targeting, and in appropriate cases efficiently transducing target cells, when incorporated in particles of the invention at the site specified is considered unexpected. The finding enables the use of techniques such as phage display libraries (Scott and Smith (1990) Science. 249:386–390) for identifying peptides useful in targeting particles of the invention.

Phage display technology permits the identification of linear peptides that bind to specific ligands.

By way of example, a phage display library may be used to identify a peptide capable of binding to the CD34 glycoprotein present on the surface of haematopoietic precursor cells, so that particles of the invention may be prepared incorporating that peptide, capable of infecting haematopoietic stem and/or progenitor cells. These cells can for example be purified and concentrated from blood using apheresis techniques. Therefore, ex vivo infection of haematopoietic stem cells with modified retroviruses capable of binding and infecting these cells could be performed. Transfusing the transduced stem cells back into the blood stream will deliver the engineered cells back to the bone marrow where they will lodge. The stem cells are self-perpetuating and therefore will provide a never ending population of engineered haematopoietic cells.

Similar selection of peptides enables the preparation of particles of the invention targeted to tumour cells expressing known receptors or proteins.

As mentioned above, the capsid of the particle of the invention may carry nucleic acid, for example packaged RNA which encodes a protein or proteins capable of being expressed within the infected host cell. RNA sequence or sequences to be packaged within the GAG and ENV proteins, require recognition sequences for effecting such packaging, and a promoter sequence for driving transcription of the RNA. Typically the transcription unit producing packaged RNA must include terminally redundant R regions, a U5 region at the 5' end and a U3 region at the 3' end, a packaging signal sequence, a tRNA primer binding site, a polypurine tract and a promoter sequence to drive the transcription unit containing the above elements. Such control sequences effect the packaging of the packageable sequence and ensure the reverse transcription and integration of the packageable RNA into the host cell. A packaging signal sequence is a nucleic acid sequence, which in the case of retroviruses has been mapped close to the 5' Long Terminal Repeat (LTR), and which on recognition by a component of the viral particle results in the encapsidation of the viral RNA, and as such may also be termed the encapsidation signal sequence. U3, R and U5 are the three regions of the LTR which contain the signals that control initiation and processing of viral transcripts.

According to another aspect of the invention there is provided a method for preparing a plurality of proteinaceous particles of the invention, which method comprises expressing within a host cell (i) self-assembling capsid proteins, (ii) ecotropic Murine Leukemia virus envelope proteins, said ENV proteins modified in that a peptide which binds to a non-murine cell is inserted in, entirely replaces, or replaces a portion of the native SEQ ID NO: 1 of the VRA region, and optionally, (iii) packageable RNA, and then culturing the host cells and harvesting the resultant budded particles.

The invention also provides a pharmaceutical composition comprising a plurality of particles according to the invention, together with a pharmaceutically acceptable carrier, for example a sterile physiologically acceptable liquid vehicle, for parenteral administration.

An embodiment of the invention will be further described by way of non-limiting illustration in the following examples and with reference to the accompanying Figures, in which:

FIG. 1. represents a predicted flexibility plot of the VRA region of MLV gp70 (SU) protein. Flexible regions were identified using the FLEXPRO program and the potential peptide insertion sites are shown as I and II. Amino acid co-ordinates of gp70 are shown on the x axis.

FIG. 2. represents CLUSTAL sequence alignments of the VRA regions of ecotropic (Moloney MLV), amphotropic (isolate 4070a), polytropic (mink cell forming MLV) and xenotropic MLV envelope proteins, identifying in the ecotropic VRA domain a number of additional sequences and regions of unconserved amino acids. Conserved sequences are shown in lower case and non-conserved sequences in upper case. Potential peptide insertion sites I and II are boxed.

FIG. 3. represents a schematic diagram of the general strategy for construction of the envelope hybrids.

FIG. 4A, 4B and 4C represents Western immunoblot analysis of viruses containing hybrid envelopes FIG. 4A. Cytoplasmic cell fractions, FIG. 4B and FIG. 4C sucrose gradient purified vial particles. Apparent molecular weights (Kd) are marked on the left of the filters. Filters 4A and 4B were probed with a polyclonal MLV env antiserum (Quality Biotech Inc, Catalogue number 04-0109), and filter 4C with an MLV gag antiserum. Detected MLV gene products are indicated. Envelope plasmids designated pRV* correspond to the plasmids described herein with pHIT* nomenclature.

MATERIALS AND METHODS

The techniques of genetic manipulation used in the construction of the modified envelope and for transient expression of host cells, are well known to those skilled in the art of genetic engineering and Cell Biology. A description of the techniques used can be found in "Molecular cloning-A laboratory manual, second edition" By J. Sambrook, E. F. Fritsch and T. Maniatis published by Cold Spring Harbor Laboratory, Box 100, New York. Additional and modified methodologies are outlined below.

Cell Lines

The human U937 (VLA-3+, VLA-4+ and VLA-5+) cell line was grown in RPMI 1640 supplemented with 10% fetal calf serum and 1 mM L-glutamine. The human renal embrionic 293T (293/tsA1609neo) (DuBridge et al. (1987) Mol. Cell. Biol. 7:379–387)293T cells were obtained from D. Baltimore (Rockefeller University), the human fibrosarcoma HT1080 cells (ATCC CCL 121), and NIH3T3 cells (ATCC) were grown in Dulbecco's modified Eagle's medium (DMEM; Gibco-BRL) supplemented with 10% (v/v) fetal calf serum and 1 mM L-glutamine, and supplemented with antibiotics.

Monoclonal Antibodies and Antisera

The purified monoclonal anti-VLA4 antibody, 2B4 was provided by Dr. Rod Pigott (British Biotech Pharmaceuticals Ltd.).

Transient Transfection, Infection and Determination of Viral Titer

Transient transfections were performed by overnight calcium phosphate treatment (Gorman et al. (1982) Mol. Cell. Biol. 32:1044–1051) on 10 cm dishes seeded the previous day to give a maximum of 50% confluence per plate on the day of transfection. 10 $\mu$9 of each plasmid (30 $\mu$g total) was used for each transfection. The transfected cells were incubated at 37° C. (5% C02) for 12 hours and the media was replaced with 5 ml of fresh media containing 10 mM sodium butyrate. The viral supernatants were harvested 12 hours later (48 hours post transfection), filtered through 0.45 $\mu$m filters and titered by infection on NIH3T3 cells.

For infections, the NIH 3T3 cells were plated onto six-well culture dishes at a density of $1–2\times10^5$ cells per well the day before infection. 1 ml of viral supernatant (at appropriate dilutions of the original stock) was added to each well with 8 $\mu$g/ml Polybrene and incubated for two hours, followed by the addition of 1 ml of fresh media. 24 hours later, the cells were split 1:4 and seeded onto 5 cm dishes. Viral titer was determined by X-gal staining. X-gal staining was performed as previously described (Sanes et al. (1986) EMBO J. 5:3133–3142) 24 hours following the 1:4 split.

Virus titer was determined by multiplying the total number of β-gal positive cells by 2, to account for the two-fold increase in cells during the infection period and the 1:4 split.

Cell Transduction 1 ml of viral supernatant (or appropriate dilutions) were added to 1×10⁶ cells with 8 µg/ml of polybrene. In the case of suspension cells, these were harvested and resuspended in the viral supernatant. The cells were incubated for 24 hours, 2 ml of fresh media added, and viral titre determined 24 hours later by X-gal staining. Target cell lines were chosen on the basis of integrin expression. VCAM binds to the VLA4 receptor, whereas RGD containing peptides like FLA16 bind to numerous integrins including VLA3 and VLA5. The U937 cell line, a human histiocytic lymphoma monocyte line, expresses VLA3, VLA4 and VLA5 and therefore should be permissive for hybrid viruses containing both the VCAM and FLA16 ligands. HT1080, a human fibrosarcoma cell line, expresses VLA5 and should only be infected by FLA16 containing viruses. The viruses were also titred on the mouse NIH 3T3 line to measure the relative efficiency of virus production.

Peptide Blocking

Peptides were synthesised using standard techniques known in the art.

Peptide blocking experiments were carried out by incubation of cells prior to infection with appropriate peptide concentration (200 µg/ml) for 1 hour at 37° C.

EXAMPLE 1

Determination of the Potential Peptide Insertion Site

In order to determine the site in the Moloney murine leukemia ecotropic envelope surface glycoprotein gp70 for positioning of the integrin binding peptide sequences, two criteria were imposed. Firstly the region should be flexible and may therefore be able to accommodate disulphide constrained peptide sequences and secondly that the region is non-conserved in related viruses and therefore is unlikely to be an important structural component of the envelope. Predicted flexibility of the envelope VRA region (the first variable region), that is thought to form part of the natural receptor binding domain (Battini et al. ;ibid. ), was determined using the FLEXPRO (Karplus, P. A., and Schulz G. E. (1985) Naturwissenchaften. 2:212–213) program and variability was assessed using CLUSTAL Higgins (1989) Cabios 5:151–153) comparing ecotropic (Shinnick etal.; ibid. ), amphotropic (Sorge et al. (1984) Mol. Cell. Biol. 4:1730–1737), polytropic (Chattopadhyay et al. (1989) Virology 168:90–100), and xenotropic (Mosey et al. (1990) Virol 64:5491–5499) MLVs (FIG. 2).

A site for insertion of targeting peptides, satisfying both the flexibility and non-conserved amino acids criteria, was identified as site 1 in FIGS. 1 and 2.

The site I sequence (SEQ ID NO: 1) is flanked by cysteine residues which may be capable of forming a disulphide bond, looping-out the intervening sequence.

Mammalian expression plasmid constructs encoding mutant ecotropic MLV envelope, containing an integrin targeting peptide replacing site 1, were constructed and co-transfected with vectors encoding the other MLV packaging components gag-pol and also a packageable retroviral genome encoding lacZ gene. Virus produced was capable of transducing mammalian cells at high efficiency.

Construction of Mutant Ecotropic Envelope Genes

The complete Moloney Murine Leukemia virus sequence is found in Shinnick et al. (1981) Nature. 293:543–548.

Oligonucleotides were synthesised according to standard techniques known in the art.

The constructs utilised for transient mammalian cell expression and retrovirus production, or for the construction of the mutant envelopes, are adequately described in Soneoka et al. (1995) Nucleic Acids Res. 23:628–633, incorporated herein by reference.

A polymerase chain reaction (PCR) cloning strategy was devised to replace precisely site I in the VRA region of ecotropic MLV gp70 with receptor-binding peptide sequences from laminin A chain, known as FLA16 (SEQ ID NO: 3), that binds to several integrins including VLA3 and VLA5 (Aumailley et al. (1990) FEBS Lett. 262, 82–86), and the minimal binding sequence from vascular adhesion molecule 1 (VCAM-1; SEQ ID NO: 2) which binds to VLA4 (Jones et al. (1995) Nature. 373:539–544).

The envelope regions immediately 5' and 3' to the insertion site in the N-terminal coding region of gp70 were generated by PCR with the addition of the peptide coding sequence. Hybrid envelopes containing the peptide binding sequences were constructed using PCR (Innis et al. (1990) PCPs Protocols: A Guide to Methods and Applications. Academic Press 177–183) to precisely replace sites I with the integrin receptor binding sequences.

Plasmid pHIT123 (Soneoka et al. ; ibid. ), which contains the ecotropic envelope gene was used as a template.

Two oligonucleotides, 5'-GCCGAATTCATGGCGCGTTCAACGCTCTCAAAA-3'(SEQ ID NO: 4) and 5'-GACCGAATTCCTATCTGAGTCGGATCCCAAATG-3' (SEQ ID NO:5) were located at the 5' end of the envelope coding sequence and just downstream of the BamHl restriction site which is at nucleotide 761 of the gp70 coding sequence (Shinnick et al.; ibid). For the construction of pHIT507 (FLA-16 peptide at site 1), two fragments were made by PCR. A 5' fragment was made by using the SEQ ID NO:4 primer and a hybrid primer 5'ACCTTGGGGAT-TATCGCCTCTTAAGGCAAAAGTAGCAC-CTTGGCAAC AAGGGGGCCCCGG-3'(SEQ ID NO:6) containing the 18 nucleotides of pHIT123 immediately upstream of site I and 42 nucieotides of the FLA16 coding sequence. A 3' fragment was amplified by using a hybrid primer 5'-CMGGTGCTACTTTTGCCTTMGAGGCGATMTCCC CMGGTTGTTCC AGAGACTGCGAA-3'(SEQ ID NO: 7) containing the 18 nucleotides of pHIT123 immediately downstream of the site I and the 42 nucleotides of FLA16 and SEQ ID NO:5 primer. The two PCR products were then used as primer/templates in a further round of PCR with the SEQ ID NO: 4 and SEQ ID NO: 5 primers to generate the N-terminal region containing the VRA-FLA16 hybrid in site 1.

A similar strategy was used to construct the other hybrid (VCAM-1 peptide at site 1). For this hybrid, oligonucleotides 5'-ATTCAGGGGGGAATCAATTTGAGTGCA CAAGGGGGCCCCGG-3'(SEQ ID NO: 11) and 5'-ACTCAAATTGATTCCCCCCTGAATTGTTCCAGAG ACTGCGAA-3'(SEQ ID NO: 12) were used in conjunction with SEQ ID NOs: 4 and 5 as above.

These N-terminal mutant ecotropic MLV products were digested with BamHI and EcoR1, purified and then ligated into the plasmid pGEM-T (Promega). The N-terminal mutant MLV fragment was then released from this plasmid as a SalI/BamHI fragment and purified. The C-terminal coding region of ecotropic MLV gp70 fragment was released from plasmid pHIT123 as a BamHI/EcoRI fragment and purified. The SalI/BamHI N-terminal mutant MLV gp70 and C-terminal MLV gp70 BamHI/EcoRI DNA fragments were ligated into the SalI/EcoR1 cut CMV expression vector pGW1 HG (described in example 1 of WO 91/09118), which also contains an SV40 origin of replication, to generate the complete modified env genes. The constructions were verified by sequencing.

FIG. 3 represents the general strategy for construction of the modified envelope genes.

The plasmid containing the hybrid envelope with FLA16 at sites I is designated pHIT507. The plasmid containing the hybrid envelope with the VCAM-1 sequence at sites I designated pHIT509.

Transfection of 293T Cells to Generate Virus

Transducing viruses containing the hybrid and control ecotropic (Moloney MLV) (Shinnick et al. (1981) Nature. 293:543–548), and amphotropic (isolate 4070a) (Sorge et a/. (1984) Mol. Cell. Biol. 4:1730–1737) envelopes were produced by transient transfection using a three-plasmid transient system in 293T cells (Soneoka et al. (ibid.).

Plasmids pHIT507, pHIT509, pHIT123 (ecotropic) and pHIT456 (identical to pHIT123 but with the amphotropic env gene replacing the ecotropic env gene) were co-transfected with pHIT60, a plasmid encoding the gag-pol products of MLV, and pHIT111, a retroviral vector carrying the lacZ reporter gene (Soneoka et al. (ibid.).

Expression of the hybrid envelopes and incorporation into the virus was determined by sucrose gradient analysis and Western blot. Western blot analysis was carried out as described in Towbin et al. (1979) Proc. Natl. Acad. Sci. U.S.A. 76:43504354. Samples were analysed by electrophoresis on 12% SDS polyacrylamide gels and transferred to nitrocellulose. Filters were probed with env antiserum (Quality Biotech Inc, Catalogue number 04–0109) at 1:3000 and bound antibody detected with horseradish peroxidase conjugated rabbit anti-goat (Sigma) antibody at a dilution of 1:2000, or gag antibody and detecting goat anti-rabbit antibody (Sigma) at 1:1000. Detection was carried out using the ECL kit (Amersham). Cytoplasmic cell fractions and purification of viral particles were prepared as previously described (Griffiths et al. (1993) J. Virol. 67:3191–3198).

Figure 4:
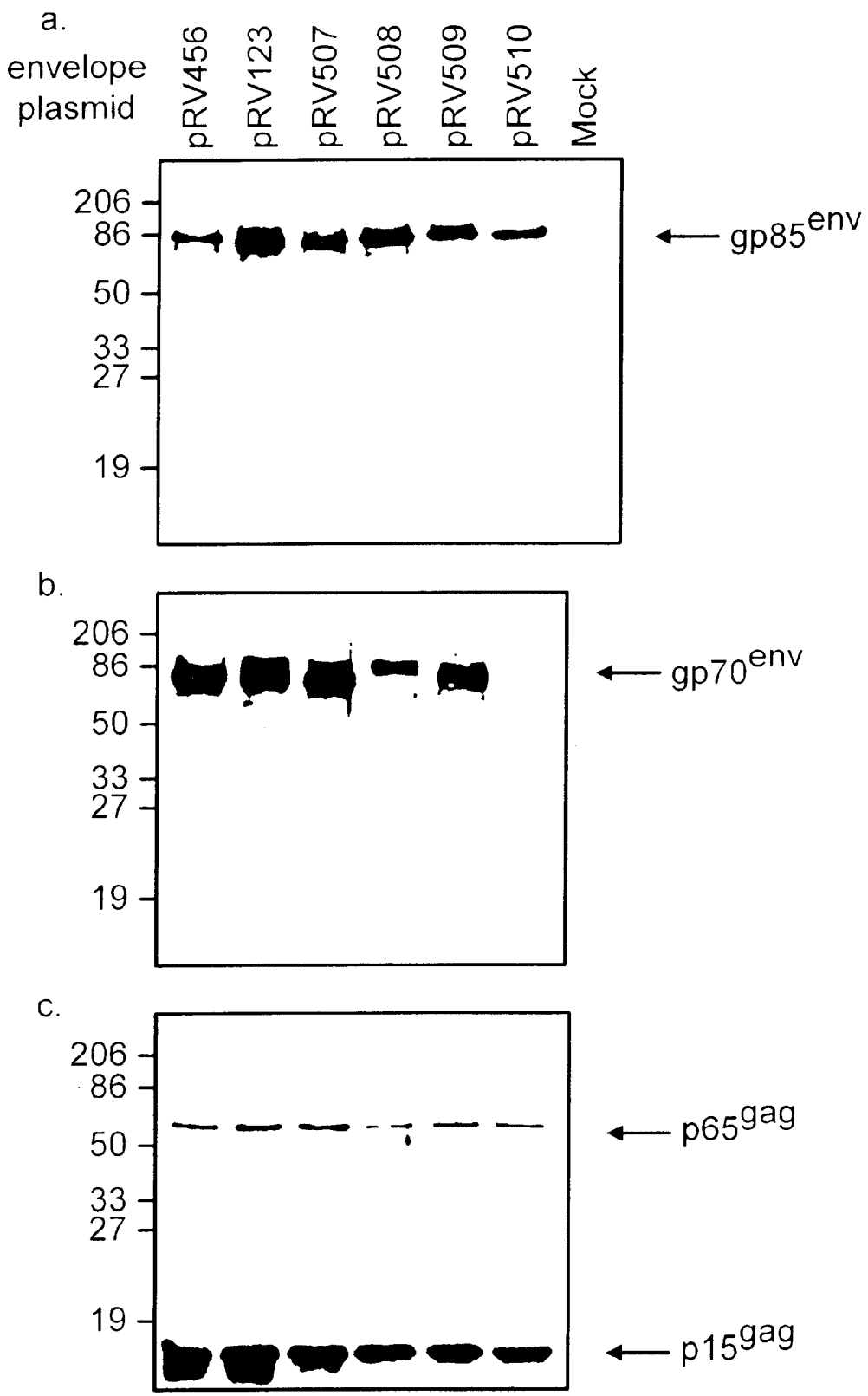

Both hybrid envelopes were produced at the same levels as the ecotropic parental envelope (FIG. 4A). The hybrids were incorporated into virus particles at the same level as the ecotropic envelope and they were processed to produce the gp70-peptide hybrid surface protein and the transmembrane protein p15e.

Transduction of Mammalian Cells

In order to test the possibility that the hybrid envelopes would target their cognate viruses to new cell types viral supernatant stocks were used to transduce U937 cells, a human histiocytic lymphoma monocyte line (Sundstrom and Nilsson (1976) Int. J. Cancer. 17:565–577). This cell line expresses VLA3, VLA4 and VLA5 and therefore should be permissive for hybrid viruses containing both the FLA16 and VCAM-1 ligands. Titres were determined by X-gal staining as an assay for delivery and integration of the lacZ-containing vector genome. This was compared with titres using a standard amphotropic vector produced in the same way. In addition, titres were measured on the mouse NIH3T3 cell line (Jainchill et al. (1969) Virology. 4:549–553) to assess the relative efficiency of virus production. The virus titres are shown in Table 1. As expected U937 cells were not infected by the parental ecotropic virus (pHIT123) but they were infected by vectors bearing the broad host-range amphotropic envelope (pHIT456). In contrast to the ecotropic parent vector, the vectors bearing hybrid envelopes delivered lacZ to the U937 cells showing that the ecotropic vector had been targeted to the human cells. Surprisingly, the hybrid envelopes (pHIT507, pHIT509) delivered lacZ at efficiences comparable with the amphotropic virus (pHIT456). In addition to delivering lacZ to the human U937 cells the hybrid viruses retained their ability to infect murine NIH3T3 cells.

In addition, a human fibrosarcoma cell line, HT1080 (Rasheed et al. (1974) Cancer. 33:1027–1033) which expresses VLA5, was infected by virus produced with pHIT507 but not with the virus produced with pHIT509 containing the VLA4 specific VCAM sequence.

TABLE 1

Viral titers from U937, HT1080 and NIH 3T3 cells transduced with parental or hybrid viruses. Titers shown are an average of 2 experiments.

| | Cell Line | | |
|---|---|---|---|
| Virus Envelope Type | U937 | HT1080 | NIH3T3 |
| pHIT456 (amphotropic) | $5.3 \times 10^4$ | $4.6 \times 10^4$ | $4.6 \times 10^5$ |
| pHIT123 (ecotropic) | negative | negative | $2.2 \times 10^5$ |
| pHIT507 (FLA16, at site 1) | $1.1 \times 10^4$ | $1 \times 10^4$ | $5.5 \times 10^5$ |
| pHIT509 (VCAM, at site 1) | $1.4 \times 10^4$ | negative | $1.1 \times 10^5$ |

Inhibition Studies

In order to demonstrate that the hybrid viruses were targeted to the human cells specifically via the peptide ligand/receptor interaction, U937 cells were incubated, prior to infection, with peptides corresponding to the FLA16 and VCAM sequences inserted into the viral envelopes. These peptides specifically blocked transduction by virus produced with pHIT507 and pHIT509 respectively but did not block transduction with the amphotropic vector.

Similarly a smaller blocking peptide, RGDS (SEQ ID NO:15), was shown to block infection by virus produced with pHIT507 in both U937 cells and HT1080 cells, thereby demonstrating the RGD specificity of the FLA16 mediated targeted gene delivery.

To further demonstrate the specificity of the hybrid viruses, infections of U937 cells were carried out in the presence of a VLA4 specific monoclonal antibody (2B4) known to block the VCAM/VLA4 interaction (Needham et al. (1994) Cell. Adhesion Comm. 2:87–99)). This antibody blocked transduction by virus produced with pHIT509, but did not block transduction by pHIT507 or pHIT48-derived virus. This demonstrates that virus containing the envelope produced by pHIT509 enters the cell via the VCAM/VLA4 interaction. Table 2 illustrates the results obtained from transduction of U937 cells with virus, produced with pHIT456 (amphotropic), pHIT507 and pHIT509 derived envelopes, pre-incubated with FLA16 peptide or anti-VLA4 antibody.

TABLE 2

Virus infection inhibition studies

| Envelope type | none | FLA 16 peptide | Anti-VLA4 antibody |
|---|---|---|---|
| pHIT 456 (amphotropic) | $6.6 \times 10^4$ | $5.5 \times 10^5$ | $4.0 \times 10^4$ |
| pHIT507 (FLA16 at site 1) | $1.8 \times 10^4$ | $1.0 \times 10^3$ | $3.2 \times 10^4$ |
| pHIT509 (VCAM at site 1) | $8.0 \times 10^3$ | $6.0 \times 10^3$ | $7.1 \times 10^2$ |

Taken together these data demonstrate that the modified retroviral vectors are capable of high efficiency targeted gene delivery via specific receptoriligand interactions. Remarkably, the efficiency of this system is approximately the same as wild-type amphotropic vectors that are used for current gene therapy trials. This means that in optimised conditions it should be possible to produce targeted vectors at titres suitable for human gene therapy.

COMPARATIVE EXAMPLE

The above example describes an embodiment of the invention. When hybrid envelopes comprising targeting peptides inserted at site 1 in the VRA region of the ecotropic MLV envelope are efficiently processed and incorporated onto the virus particles, they can then direct the virus to cells expressing specific integrins on their surface and efficiently infect these cells.

By way of comparison, using the same selection parameters for identifying site 1, an alternative, apparently equivalent site, designated site II in FIG. 1 and 2 was identified for insertion of heterologous targeting peptides.

The VCAM-1 derived (SEQ ID NO: 2) and FLA-16 (SEQ ID NO: 3) peptides were inserted into site 11 (SEQ ID NO:8) using a similar construction strategy to that in example 1.

In order to introduce the FLA16 peptide at site II, for the construction of pHIT508, oligonucleotides 5'-ACCTTGGGGATTATCGCCTCTTAAGGCAAAAGTAGCACCTTGACAAA AAGGGGATTGATATTCTAGCCC-3'(SEQ ID NO:9) and 5-TGTCAAGGTGCTACTTTTGCCTTAAGAGGCGATAATCCCCAAGGTTGTTGCTCAGG GGGCAGCAGCCCAGGC-3'(SEQ ID NO:10) were used in conjunction with SEQ ID NOs: 4 and 5 as in example 1. For the construction of pHIT510 (VCAM-1 peptide at VRA site II), oligonucleotides 5'-ATTCAGGGGGGAATCAATTTGAGTACAAAAAGG GGATTGATATTCTAGCCC-3'(SEQ ID NO: 13) and 5'-ACTCAAATTGATTCCCCCCTGAATTGTTGCTCAG GGGGCAGCAGCCCAGGC-3'(SEQ ID NO: 14) were used in conjunction with SEQ ID NOs: 4 and 5 as in example 1.

As in example 1 (supra), these N-terminal mutant ecotropic MLV products were digested and then ligated to the C-terminal coding region of ecotropic MLV gp70. The plasmid containing the hybrid envelope with FLA16 at sites II is designated pHIT508. The plasmid containing the hybrid envelope with the VCAM-1 sequence at sites II is designated pHIT510.

As in example 1, virus was produced by transient transfection of 293T cells. Expression of the hybrid envelopes and incorporation into the virus was determined by sucrose gradient analysis and Western blot. Both hybrid envelopes were produced at the same levels as the ecotropic parental envelope (FIG. 4A), but unlike the hybrid envelopes produced in example 1, the envelopes with the peptide insertions at site II were incorporated into virus particles at much lower efficiencies and were not processed (FIGS. 4B and 4C) suggesting that changes in this region may result in substantial alterations in the function of the protein.

Virus produced with the peptides inserted at site II were tested in the transduction studies as in example 1. The virus titres are shown in Table 3.

TABLE 3

Viral titers from U937, HT1080 and NIH 3T3 cells transduced with site II hybrid viruses. Titers shown are an average of 2 experiments.

| | Cell Line | |
|---|---|---|
| Virus Envelope Type | U937 | NIH3T3 |
| pHIT508 (FLA16, at site II) | $1.5 \times 10^2$ | $2.0 \times 10^2$ |
| pHIT510 (VCAM, at site II) | $1.5 \times 10^2$ | $4 \times 10^2$ |

Results from this comparative example demonstrate that although site II was identified using the same parameters of flexibility and non-conservative amino acids as used for identifying site 1, the site 11 hybrid envelopes are not processed nor incorporated into virus particles as efficiently as the site I hybrid envelopes. Additionally, virus containing the hybrid site II envelopes were only capable of infecting mammalian cells at titres of about $10^2$. These titres are similar to the infection results obtained by Valsesia-Wittman et al. (ibid.) with their mutant RSV.

Sequence Identification Numbers (SEQ ID NOs:):

1. Ser-Gly-Gly-Ser-Ser-Pro-Gly
2. Cys-Thr-IIe-Asp-Ser-Pro-Leu-Asn-Cys
3. Cys-Gln-Gly-Ala-Thr-Phe-Ala-Leu-Arg-Gly-Asp-Asn-Pro-Gin-Gly-Cys
4. 5'-GCCGAATTCATGGCGCGTTCMCGCTCTCAAAA-3'
5. 5'-GACCGAATTCCTATCTGAGTCGGATCCCAAATG-3'
6. 5'-ACCTTGGGGATTATCGCCTCTTMGGCAAAAGTAGCACCTTGGCAACAAGGGGGCCCCGG-3'
7. 5'-CAAGGTGCTACTTTTGCCTTAAGAGGCGATAATCCCCAAGGTTGTTCCAGAGACTGCGM-3'
8. Ser-Ser-Pro-Pro-Gly-Pro-Pro
9. 5'-ACCTTGGGGATTATCGCCTCTTAAGGCAAAAGTAGCACCTTGACAAAAAGGGGATTGATATTCTAGCCC-3'
10. 5'-TGTCAAGGTGCTACTTTTGCCTTMGAGGCGATAATCCCCAAGGTTGTTGCTCAGGGGGCAGCAGCCCAGGC-3'
11. 5'-ATTCAGGGGGGAATCAATTTGAGTGCACMGGGGGCCCCGG-3'
12. 5'-ACTCAAATTGATTCCCCCCTGAATTGTTCCAGAGACTGCGAA-3'
13. 5'-ATTCAGGGGGGAATCAATTTGAGTACAAAAAGGGGATTGATATTCTAGCCC-3'
14. 5'-ACTCAAATTGATTCCCCCCTGATTGTTGCTCAGGGGGCAGCAGCCCAGGC-3'
15. Arg-Gly-Asp-Ser

What is claimed is:

1. A proteinaceous particle comprising a capsid enveloped by ecotropic Murine Leukemia Virus (MLV) envelope (ENV) proteins, wherein a heterologous peptide which binds to a non-murine cell receptor is inserted in, entirely replaces, or replaces a portion of the native SEQ ID NO: 1 of a VRA region of said envelope proteins, and wherein said peptide binds one or more integrins and comprises SEQ ID NO:2.

2. A proteinaceous particle according to claim 1, wherein the capsid contains RNA.

3. A proteinaceous particle according to claim 2, wherein the RNA encodes a gene or genes which are expressed within an infected host cell.

4. An ecotropic Murine Leukemia Virus (MLV) envelope (ENV) protein, wherein a heterologous peptide which binds to a non-murine cell receptor is inserted in, entirely replaces, or replaces a portion of the native SEQ ID NO: 1 of a VRA region of said envelope protein, and wherein said peptide binds one or more integrins and comprises SEQ ID NO:2.

5. A pharmaceutical composition comprising a plurality of proteinaceous particles according to claim 1 together with a pharmaceutically acceptable carrier.

6. A pharmaceutical composition according to claim 5, wherein the pharmaceutically acceptable carrier is a sterile physiologically acceptable liquid vehicle for parenteral administration.

7. A proteinaceous particle comprising a capsid enveloped by ecotropic Murine Leukemia Virus (MLV) envelope (ENV) proteins, wherein a heterologous peptide which binds to a non-murine cell receptor is inserted in, entirely replaces, or replaces a portion of the native SEQ ID NO: 1 of a VRA region of said envelope proteins, and wherein said peptide is not more than 30 amino acids long and comprises SEQ ID NO:2.

8. A proteinaceous particle according to claim 7, wherein the capsid contains RNA.

9. A proteinaceous particle according to claim 8, wherein the RNA encodes a gene or genes which are expressed within an infected host cell.

10. An ecotropic Murine Leukemia Virus (MLV) envelope (ENV) protein, wherein a heterologous peptide which binds to a non-murine cell receptor is inserted in, entirely replaces, or replaces a portion of the native SEQ ID NO: 1 of a VRA region of said envelope protein, and wherein said peptide is not more than 30 amino acids long and comprises SEQ ID NO:2.

11. A pharmaceutical composition comprising a plurality of proteinaceous particles according to claim 7 together with a pharmaceutically acceptable carrier.

12. A pharmaceutical composition according to claim 7, wherein the pharmaceutically acceptable carrier is a sterile physiologically acceptable liquid vehicle for parenteral administration.

* * * * *